United States Patent [19]

Ness

[11] 4,067,337
[45] Jan. 10, 1978

[54] RE-USABLE TAPE TAB FOR DISPOSABLE DIAPERS

[75] Inventor: Irving Stanley Ness, Princeton, N.J.

[73] Assignee: Johnson & Johnson, New Brunswick, N.J.

[21] Appl. No.: 659,313

[22] Filed: Feb. 19, 1976

[51] Int. Cl.² .......................................... A61F 13/16
[52] U.S. Cl. ................................... 128/287; 128/284; 24/67 AR
[58] Field of Search .................. 128/287, 284, 156; 24/DIG. 11, 67 AR

[56] References Cited

U.S. PATENT DOCUMENTS

| 2,399,545 | 4/1946 | Davis | 128/156 |
| 2,740,403 | 4/1956 | Schueler | 128/156 |
| 3,810,472 | 5/1974 | Aldinger et al. | 128/287 |
| 3,811,438 | 5/1974 | Economou | 128/156 |
| 3,853,129 | 12/1974 | Kozak | 128/287 |
| 3,870,041 | 3/1975 | Davies | 128/156 |
| 3,967,624 | 7/1976 | Milnamow | 128/284 X |

Primary Examiner—Stephen C. Pellegrino

[57] ABSTRACT

An adhesive tape tab for use on disposable diapers which may be peeled and re-used for subsequent fastenings of the diaper without tearing the outside plastic film of the diaper or the tape tab itself. The tape tab has a tape which is fastened on one portion to the diaper. A second, extendable portion of the tape has adhesive material thereon, however, the adhesive material is interrupted and divided into segments by nonadhesive areas formed by a nonadhesive open-mesh sheet material. Each of these adhesive segments has an area so that when the second portion of tape is attached to the outside film the peel strength between tape and film over the segmented area is less than the tearing strength of the film over the same segmented area.

7 Claims, 7 Drawing Figures

U.S. Patent  Jan. 10, 1978  Sheet 1 of 2  4,067,337
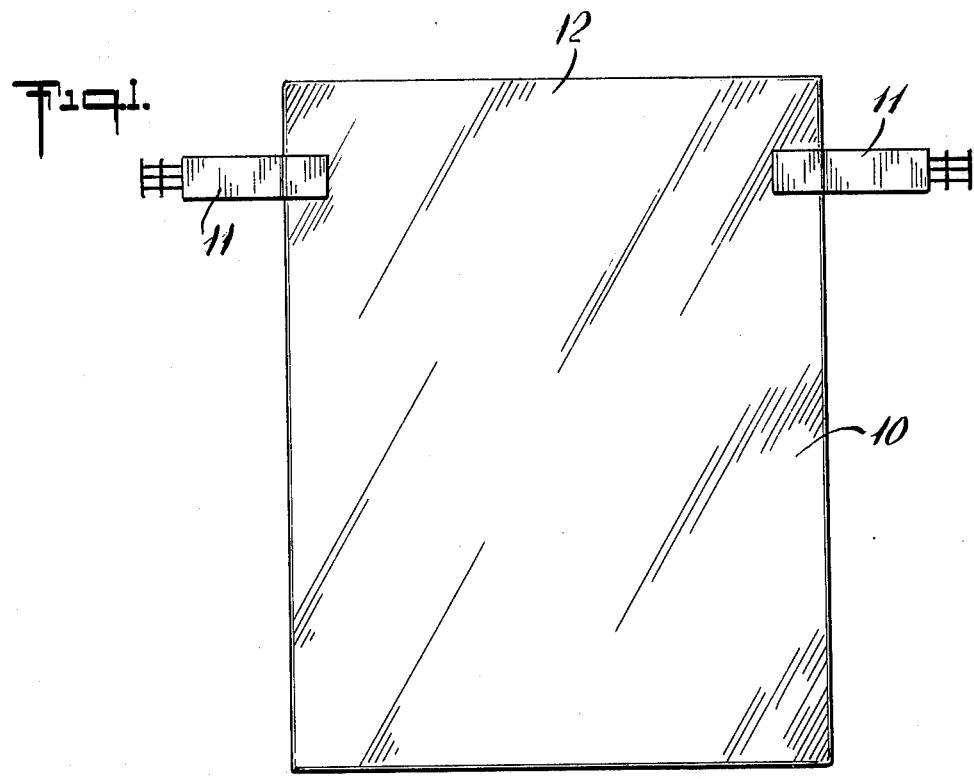
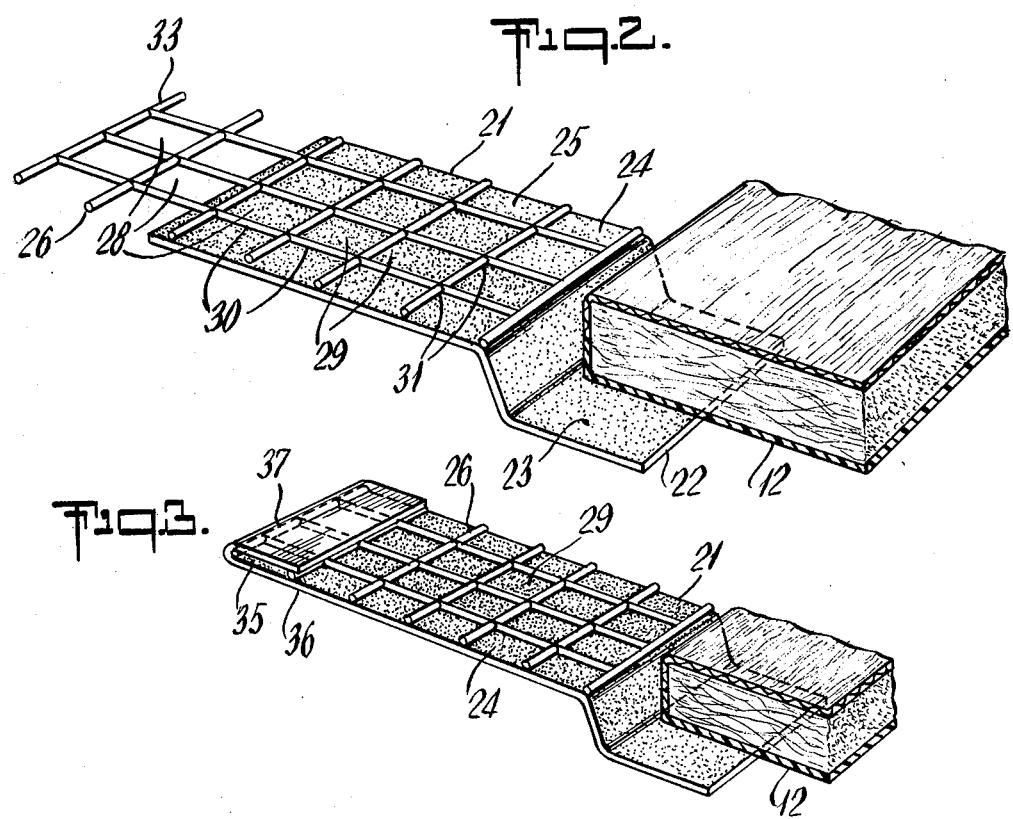

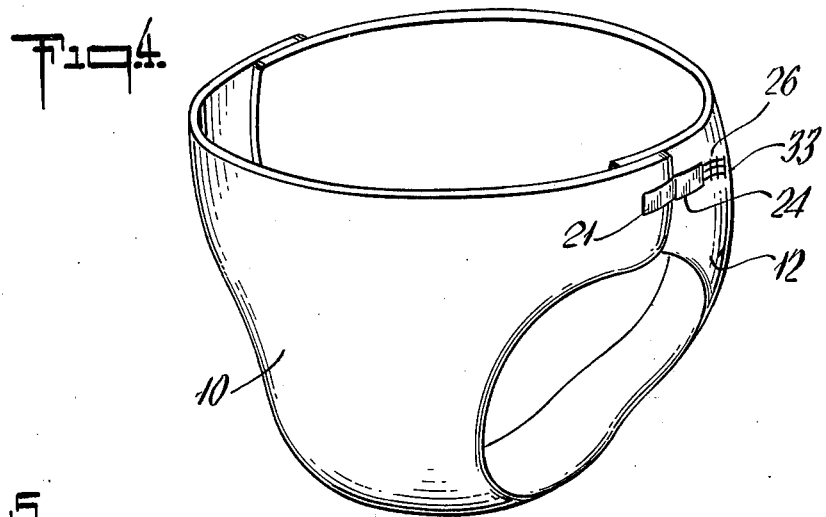
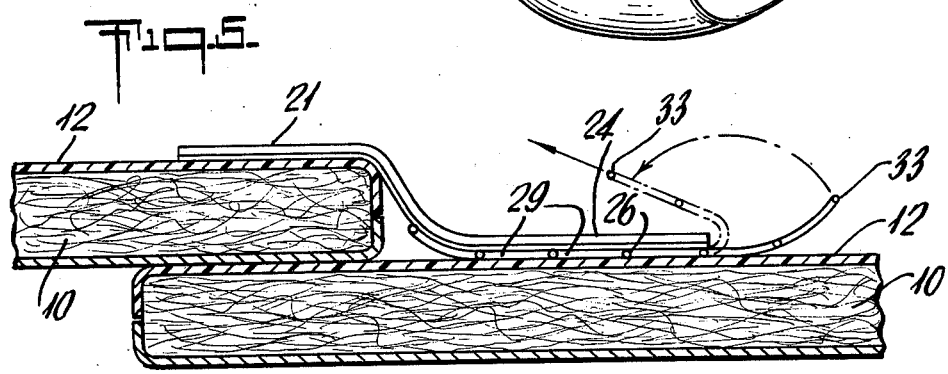
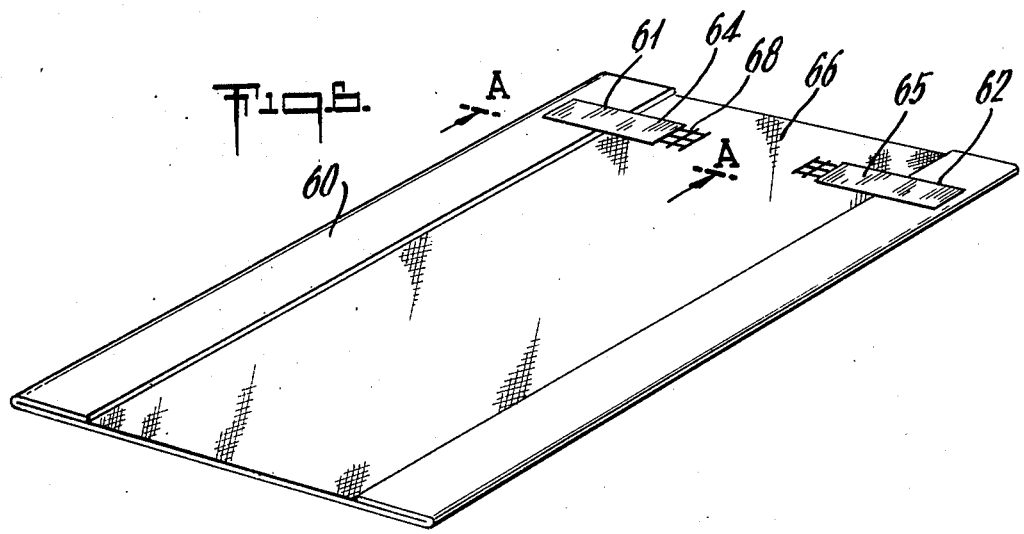
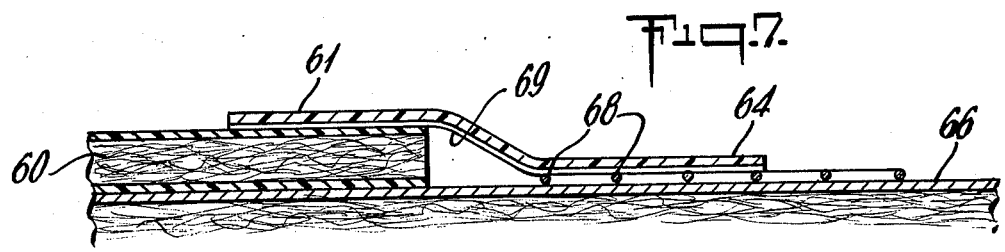

RE-USABLE TAPE TAB FOR DISPOSABLE DIAPERS

BACKGROUND OF THE INVENTION

This invention relates to an improved adhesive tape tab for use on disposable diapers. More particularly, this invention relates to an improved adhesive tape tab which permits a disposable diaper to be opened after a closure has been made without tearing the outside film of the diaper or the tape tab itself, and which can be repositioned and re-used for subsequent fastenings of the diaper.

It has become very common and practical to use adhesive tape tabs on disposable diapers. The practicality of tape tabs, rather than pins, is self-evident. However, there are shortcomings in the use of adhesive tape tabs which also become evident especially when the diaper needs checking for soiling or for repositioning. For instance, when a child reaches the stage of toilet training the diaper must be opened and removed, and if not soiled, could be used again. The prime or major shortcoming in the known adhesive tape tabs is the lack of easy separability from the diaper once the original closure has been made. To separate the adhesive tape tab from the surface of the diaper on most, if not all, occasions either the outside surface of the diaper, usually a thin, plastic film, is torn or the tape tap itself is torn. A torn tape tab or a torn diaper outside surface makes refastening very cumbersome if not, practically, impossible. Furthermore, the consumer has had to discard unsoiled diapers because the attempt to open the diaper has torn the outside of the diaper too much to make a subsequent closure. This lack of re-use is an economic disadvantage and an expensive burden due to the cost of disposable diapers.

The tearing problem arises from use of a very thin plastic film as the outside surface on nearly all disposable diapers. This plastic film, being thin, is economical, flexible, somewhat supple, and most importantly, is impermeable so as to act as a fluid barrier for retaining fluids within the diaper. While the known adhesive tape tabs make a good, reliable fastening on this film when the diaper is in use, the thin nature of the film allows the film to easily tear when attempts are made to peel the tapes from the film. Of course, making the plastic films somewhat thicker is a possible means of increasing the strength of the film in order to permit an adhesive tape to be peeled therefrom. However, the cost of the thicker film is increased, its flexibility and suppleness reduced, while no assurance is gained that tearing will not occur under variable tape fastening conditions.

Recently, there have been attempts to provide disposable diapers with adhesive tape tabs which can be used more than once. In U.S. Pat. No. 3,848,596, the tape tab fastening means provides an arrangement which is essentially useful for only two fastenings, the original and one more. Use of multiple release sheets on the tape tabs provides the refastening ability. The multiple release sheets are, however, limiting elements in the refastening or repositioning ability of the tapes, and add cost in the manufacture of the diapers. Besides the cost factor, the use of multiple release sheets does not overcome the problem of tearing either the outside of the diaper or the tape tab itself in order to open the diaper after the original closure has been made. In those instances when the outside diaper film is torn, the absorbent material inside the diaper is exposed, may drop out of the diaper in pieces and does not permit any neat and effective refastening of the diaper around the wearer. Consequently, the diaper has to be discarded, even though it may not be soiled.

The tape fastener disclosed in U.S. Pat. No. 3,853,129 is so constructed as to be used on disposable diapers without the need of a release paper. The tape fastener has a middle segment having a plastic material with a retiform surface; the tape is folded when the diaper is in the non-operating position so that a releasable adhesive end surface of the tape lies against the surface of the plastic material. The middle plastic segment and the shape of the fold allows the tape tab to be used without a release paper. In use, however, this tape tab with the retiform plastic material creates additional holding power against the backing sheet of the diaper and cannot be separated after closure without, on most occasions, tearing the diaper backing sheet or tearing the tab itself.

SUMMARY OF THE INVENTION

An improved, economical adhesive tape tab which can be used for opening and refastening disposable diapers on many occasions throughout the service of the diaper has now been discovered. The adhesive tape tab requires only one adhesively coated tape for utility, is not limited in the number of refastening opportunities by the number of release sheets, may be employed on presently used thin, plastic film diaper surfaces, and most importantly, can be separated from the diaper without tearing the diaper film or the tab itself.

The primary advantage of this new adhesive tape tab is the cost savings gained from using disposable diapers many times or until soiled. Especially in circumstances where the diaper has need to be opened, such as with children in the toilet-training stage, is the re-usability feature a significant advantage. In this respect one diaper may be opened and removed from the child in toilet training and re-used if not soiled. Previously, a new diaper would have had to be used since the known diaper tape tab do not accomodate the re-usability feature. Besides a cost savings, the re-use of the same diaper is a convenience measure since an additional diaper does not have to be available every time the child makes an attempt to learn the significance of the toilet.

In addition to the features mentioned above, the preferred and other embodiments of this new adhesive tape tab may be utilized on the disposable diaper without the need of a protective release sheet. Elimination of release sheets on disposable diapers overcomes the discardal problems associated with entirely removing protective release sheets while effecting a cost savings by not having to use any type of protective covering on the adhesive tape tab.

In accordance with the principles of this invention, an improved adhesive tape tab is provided for repositionable and reapplicable use on any of the well-known disposable diapers, generally having an inside surface, a thin plastic-film outside surface and an absorbent layer between said surfaces. The tape tab of the present invention has a tape with a first portion attached to one part of the diaper and a second, extendable portion for attachment to the plastic film on another part of the diaper. On one surface of at least the second portion of the tape there is an adhesive material. This adhesive material is interrupted and divided into segments by nonadhesive areas. Each of the adhesive segments is so defined by the nonadhesive areas that the peel strength between the second portion of the tape and the film to which it is attached over the segmented area is less than the tearing strength of the film over the same segmented area.

In the preferred embodiment of this invention the nonadhesive areas on one surface of at least the second portion of the tape are the filaments and intersections of a thin, flexible plastic open-mesh netting. The openings divide the adhesive material into a multiplicity of smaller segments. When the second portion of the tape is peeled from the film over these distinct, smaller adhesive segments, the tearing strength of the plastic film is not exceeded as it would be over the entire adhesive surface without being divided. As a convenient pull-tab for peeling the tape tab from the diaper this embodiment includes a segment of the plastic netting extending beyond the furthest edge of the tape.

The structure of this new adhesive tape tab permits a sealed tape to be separated from the thin, plastic film of the diaper without any tearing. Uniform distribution of peeling forces and reduced tear stress area over which the tape is peeled, provided by the segmented adhesive areas, permit a surprisingly convenient separation between tape and diaper. Such ready separability and good, strong closures upon subsequent fastenings provide the economical and practical advantages of the present invention.

BRIEF DESCRIPTION OF THE DRAWINGS

These and other advantages, features and aspects of the invention will become apparent upon reading the following detailed description and upon reference to the following drawings wherein:

FIG. 1 is a plan view of a typical disposable diaper, showing the new tape tab attached;

FIG. 2 is a bottom perspective view showing the preferred embodiment of providing nonadhesive areas on one surface of the tape;

FIG. 3 is a bottom perspective view showing another embodiment of the pull-tab section of the tape;

FIG. 4 is a perspective view showing the diaper in a fastened condition secured with the improved adhesive tape tab;

FIG. 5 is a cross-sectional view of the peeling action of the new tape tab to effectuate an opening of a closed diaper;

FIG. 6 is a perspective view depicting the positions of the new tape tabs before use without the need for protective release covers; and FIG. 7 is a cross-sectional view taken along lines A—A of FIG. 6.

DETAILED DESCRIPTION OF THE DRAWINGS

With particular reference to FIG. 1, there is shown a disposable type diaper 10 with an improved adhesive tape tab 11 attached at two places to a part of the diaper. In this instance the tabs are shown attached to the outside surface 12 of the diaper; depending upon the fold of the diaper along the sides, however, the tabs may be attached to the inside surface or at some position between the inside and outside surfaces, whatever is practicable.

A bottom perspective view in FIG. 2 shows the detailed structure of the preferred embodiment of the new adhesive tape tab. A tape 21 has a first portion 22 fastened to the outside surface 12 of the diaper. This outside surface 12 is a thin, plastic film, generally in the range of 0.00075–0.0015 inch (0.0019–0.0038 cm.) thick. Typical materials used on the outside plastic film include polypropylene, polyethylene, and the like. The first portion 22 may have an adhesive layer 23 on one surface in order to be fastened to the diaper as seen in the drawings; or, the part of the diaper to which the tape is to be attached may be adhesively treated to provide the fastening capabilities. The attachment of the tape tab to the diaper may be accomplished by any means seen fit to be employed.

Extending from the first portion 22 of tape is a second portion 24. On one surface of the second portion 24 of tape is an adhesive material 25. The adhesive material 25 covers the entire second portion 24 except for the areas which divide and interrupt the layer of adhesive material into segments as will be hereinafter described. This extendable, second portion 24 of tape with the adhesive material 25 thereon is intended to be used to fasten the diaper around the wearer. The second portion 24 is fastened to another part of the diaper by being attached to the plastic, outside film 12.

To interrupt and divide the adhesive material 25 into segments 29 a nonadhesive sheet material 26 having a multiplicity of openings 28 is attached to the adhesive surface 25 of the second portion 24 of the tape 21. This sheet material 26 may cover one entire surface of the tape 21 or just the adhesive surface 25 of the extendable second portion 24 of the tape as shown in the drawings. The multiplicity of openings 28 is formed by filaments 30 or portions of the material which border the openings. These filaments 30 may be strands of material in a structure of fabric woven in a very loose weave or scrim as to produce large openings or spaces 28 between adjacent strands. These filaments may be the land portions of a nonwoven fabric produced so as to have a flat, planar construction with a multiplicity of discontinuous openings or holes located therein.

It has been found preferable to use a sheet material 26 in which the filaments 30 are integral in nature at the junctures 31 where they intersect; i.e., the filaments 30 merge together in the same plane rather than being characterized by overlapping, or criss-crossing as might be found in a woven fabric. The more planar construction of the sheet material provides a more consistent, uniform contact between sheet materials 26 and the adhesive layer 25 on the tape; it also lies evenly against or in the adhesive layer so that the adhesive areas through the openings 28 are interrupted and divided into distinct segments 29.

The openings 28 in the sheet material 26 define the size of the distinct adhesive segments 29 on the second portion 24. It is the explicit purpose of the smaller, reduced adhesive segments 29 to reduce the area over which the second portion is to be peeled from the plastic film. Specifically, it has been mentioned above that when a standard sized adhesive tape tab is peeled from a thin plastic film tearing readily occurs. One of the causes of this tearing is that over the total area of the tape tab the peel strengh between tape tab and plastic film exceeds the tearing strength of the thin plastic film.

To rectify that problem this new tape tab is divided into smaller segments of adhesive areas 29 as seen in the drawings. Each adhesive segment 29 is separated or interrupted from adjacent adhesive segments by nonadhesive areas, in this case, the filaments 30 of the sheet material 26. When peeling the second portion 24 of the tape 21 from the plastic film 12 with the adhesive segments 29 thereon, an interrupted peeling action occurs.

The effect of the interrupted peeling is that peeling stresses which induce tearing are restricted to a much smaller area. In this respect, it has become possible to reduce the peeling strength between adhesive tape and plastic film below the tearing strength of the plastic film over that reduced area. Thus, the complete peeling action becomes a series of smaller or short peeling actions interrupted by the nonadhesive areas upon dividing the adhesive segments.

For a thin plastic film, such as a polyethylene having a thickness between 0.00075 and 0.0015 inches (0.0019 and 0.0038cm), typical tearing strengths range between approximately 1.5 and 3.0 lb/in$^2$ (105 and 210 g./cm$^2$. These values are determined by measuring the amount of force required to tear a unit area of the film when the force is applied to the film, e.g., pulling forces on the force at a 90° angle to the film. Similarly, the peel strength between an adhesive tape and the film can be determined by measuring the amount of force applied, for instance, at a 90° angle, to the tape over a given area which is required to peel the tape from the film. Of course, if the film tears, the peel strength between tape and film has exceeded the tearing strength of the film. It has been determined that when using a plastic netting sheet material 26 as the nonadhesive areas on the second portion 24 as seen in the drawings individual adhesive segments 29 having areas less than 0.250 in.$^2$ (1.61 cm.$^2$) produces a peel strength of tape to film less than the tearing strength of the film. The thickness of the plastic netting employed to provide these results lies between 0.002 and 0.012 inches (0.0051 and 0.0305 cm.).

When using the concept of this invention the reduction of the peel strength of tape to film to a safe level generally has a somewhat diminished effect on the holding strength of the tape to the diaper, with particular reference to individual adhesive segments. However, when a plurality of smaller adhesive segments is accumulated as a whole on the adhesive tape surface, there is sufficient holding strength and shear strength to maintain satisfactory performance of the adhesive tape during contemplated use. As seen in FIG. 2, the openings 28 in the netting provide a plurality of adhesive segments 29; these segments 29, while having reduced peel strength on an individual basis, provide more than adequate holding strength of the tape to diaper on a combined basis.

The shapes of the adhesive segments 29 which are defined by the nonadhesive areas on the second portion 24 of the tape may take any geometric configuration. For instance, the adhesive segments may conveniently be circles, squares, rectangles, triangles, ellipses or any other shape, provided that the area confined by the outline of those shapes can be controlled to provide the proper relationship between peel strength and tearing strength as described above.

To divide the adhesive potion of the tape into smaller segments each adhesive segment is interrupted or separated from adjacent adhesive segments by nonadhesive areas. These nonadhesive areas break up the stress area due to peeling forces and introduce sufficient discontinuity in the peeling action to confine the peeling stresses to the areas of the smaller adhesive segments. The nonadhesive areas may be gaps in the adhesive, strips of nonadhesive material on top of the adhesive surface to provide interruptions and divisions in the adhesive surface, or various other forms and means of separating the adhesive segments.

It has been found desirable and very practical to produce a plurality of smaller adhesive segments by using a nonadhesive, open-mesh sheet material or netting placed in the adhesive material on the extendable, second portion of the tape. Textile materials such as loosely woven scrim fabrics, nonwoven fabrics with a plurality of open areas, and plastic netting material with intersecting or overlapping filaments produce excellent results when used in this invention. Preferably, an open or reticulated plastic netting with integrally intersecting filament junctures is the most desirable and functional material to be used in conjunction with the adhesive tape. Reticulated plastic nettings described in U.S. Pat. No. 3,666,609 are good examples of the type of plastic sheet material which is advantageously used in the invention. These plastic products are flat, sheet-like synthetic polymers with a plurality of openings formed by filaments which are integrally joined at the intersections. The synthetic polymers preferably used to form the open sheet in this invention are the polyolefins, more particularly, polypropylene and polyethylene.

As another aspect of the present invention there is shown in FIG. 2 a segment 33 of the open sheet material which extends beyond the furthest edge of the tape 21. The segment 33 of the sheet 26 overhanging the furthest or distal edge of the second portion 24 of the tape is free, unsecured and is not covered by any adhesive. It is the purpose of this over-hanging, extending material to act as a pull-tab to aid in the peeling of the tape from the diaper after a closure has been made.

Instead of relying on the overhanging segment of the flexible sheet material to act as a pull-tab by itself, another alternative may be employed. In FIG. 3, the extendable, second portion 24 of the tape 21 is detailed. In this embodiment, a segment of the second portion 24 extends beyond the furthest or distal edge of the flexible open sheet material 26, but is folded back upon itself, covers the end portion of the flexible sheet material 26, and forms a sandwich section 35. The outside surfaces 36 and 37 of the sandwich section 35 are non-adhesive surfaces and are formed by the wrap-around of the non-adhesive surface of the second portion 24 of the tape.

When this embodiment of the pull-tab is used, the adhesive segments 29 on the tape 24 make adhesive contact to the diaper to effectuate a closing. The sandwich section 35 with non-adhesive surfaces 36 and 37 remains free and unsecured to the diaper, and is a ready pull-tab on which to grab when the tape tab is to be peeled from the diaper. The configuration of the pull-tab as depicted in this embodiment provides reinforcement of the flexible sheet material during the peeling process.

A fastened disposable diaper 10 is shown in FIG. 4, the diaper secured with the improved adhesive tape tabs. The second portion of the tape 24 which includes the open sheet material 26 is pressed against the backing sheet 12 of the diaper so that the adhesive segments exposed by the openings of the material 26 make contact with the backing sheet 12 thereby effectuating a closure. The over-hanging portion or segment 33 of the sheet material 26 is free and unsecured, and acts as a convenient pull-tab when the diaper need be opened.

The effect of the peeling action aided by the overhanging segment of open-mesh sheet material, and the advantages produced thereby, is clearly shown in FIG. 5. When a closed diaper 10 using the improved tape tab of this invention needs inspection or adjustment or whatever reason for opening, the first step is to conveniently take hold of the overhanging segment 33 of sheet material 26. By pulling the overhanging segment 33 back in the direction over the tape 21 (as shown by the arrow in FIG. 5), the second portion of the tape can be readily separated from the backing sheet 12 of the diaper. In the adhesive tape tab of this invention, the overhanging or extending open sheet material 33 on the adhesive potion tape 24 assists in peeling the second portion of tape evenly and cleanly over the stress area.

Furthermore, additional closures of the diaper can be made in the same fashion the original closure was made. Once the tape is peeled from the previously fastened positioned on the surface 12 of the diaper, the outside plastic film is not torn or ripped, and sufficient adhesive remains on the adhesive segments to be used again. The extendable, second portion of the tape can be fastened to the diaper in the same location as previous closures were made, or in a different location if a different or neater fit is required of the diaper on re-use. The tape is re-used in the same fashion an original closure is made; i.e., the tape is pressed against the fastening surface so that the adhesive portions 29 of the second portion 24 of the tape exposed by the openings in the sheet material 26 make adhesive contact on the diaper. These additional closures are strong and sufficiently adequate to hold the diaper in a fixed position during use. The convenience of the tape tab of this invention allows many openings and refastenings during the normal service of the diaper.

When the nonadhesive areas located on the extendable portion of the adhesive tape tab are raised or protrude above the adhesive material the new tab may be stored on or packaged before use without an additional protective release sheet. In FIG. 6 a typical diaper 60 is shown as it may be folded in some instances when removed from its package. Two tabs 61 and 62 are attached to the diaper 60 on the folded sides and have segments 64 and 65 extending over the edge of the folded sides. The extending segments 64 and 65 lie against the inner surface 66 of the diaper.

As seen in the embodiment of FIG. 6 and more clearly in FIG. 7, the nonadhesive areas are filaments 68 of an open mesh netting material which are embedded or pressed into the adhesive material 69 on the bottom surface of the extending portion 64 of the tape. Since the nonadhesive filaments 68 are not submerged into the adhesive material but actually protrude out of the adhesive material, the filaments 68 rest on the inner surface 66 of the diaper before use. By allowing the nonadhesive filaments to rest against the inside surface of the diaper there is no need to cover the adhesive segments of the tab with a protective release sheet. When the diaper is ready for use there is nothing, such as a release sheet, to peel or from which to peel in order to use the tape tab. The user merely lifts the tab away from its resting position and places the diaper around the wearer.

While it is feasible to utilize some embodiments of the adhesive tape tab of this invention without protective release sheets, those sheets and other means may be desirably used when convenient or suitable in order to protect the adhesive surface of the extendable portion of the tape before use.

Another advantage of the new tape tab of this invention in in the final opening of the diaper, when the diaper is ready to be discarded. The new tape tab allows the diaper to be opened cleanly, with no untidy tearing, while sufficient adhesive remains on the tape for one last function. After the diaper is removed from the wearer, it may be folded or rolled and then sealed closed with the tape tabs so that the contents are contained securely within in order to be discarded.

This invention is further illustrated by the following Examples which should not, however, be construed as fully delineating the scope of this discovery.

EXAMPLE I

An adhesive tape tab for use on disposable diapers is formed by attaching a flat, open planar sheet of plastic netting material with integrally intersecting intersections to an adhesively treated surface of a tape. The plastic sheet material is made of polypropylene and is attached to the portion of the tape which is extendable beyond the edge of the diaper; the plastic sheet material also has a segment extending beyond the distal or furthest edge of the tape. The plastic sheet contains openings in the form of rectangles, each rectangle having an open area of approximately 0.041 square inches (0.264 sq. cm.). The thickness of the plastic sheet is approximately 0.005 inches (0.0127 cm). The openings of the plastic sheet material form adhesive segments in the extendable potion of the tape.

The extendable portion of tape is attached to the outside surface of the diaper which is made of polyethylene film, 0.001 inch (0.0025 cm.) thick. The tearing strength of the polyethylene film is approximately 2.0 lb/in$^2$ (140g./cm$^2$). The extendable portion of tape is readily peeled from the polyethylene films, since the peel strength between the tape and the film over the individual adhesive segments is less than the tearing strength of the film over the same individual adhesive segments.

EXAMPLE II

The open plastic netting of Example I is attached the tape such that the longitudinal filaments of the sheet form an angle of 45° with the longitudinal direction of the tape. The openings in the length and width-wise directions of the sheet are the same as in Example I.

The tape tab with this open plastic sheet makes an excellent closure on the diaper during use and is readily separated when diaper checking, repositioning or the like is required.

Thus, it is apparent that there has been provided, in accordance with the invention, an improved, reusable adhesive tape tab for use on disposable diapers that fully satisfies the aims, advantages and aspects set forth above. While the invention has been described in conjunction with specific embodiments thereof, it is evident that many alternatives, modifications and variations will be apparent to those skilled in the art in view of the foregoing description. Accordingly, the plenary invention is intended to embrace all such alternatives, modifications and variations as fall within the spirit and broad scope of the described invention.

What is claimed is:

1. In a disposable diaper of the type having an inside surface and an absorbent layer between said surfaces, and an adhesive tape tab for repositionable and reapplicable use on said diaper, said adhesive tape tab having a first portion attached to one part of the diaper and having a second extendable portion for attachment to said outside film on another part of the diaper; adhesive material on one surface of the second portion of said adhesive tape tab, said adhesive material being interrupted and divided into segments by filaments and intersections of a nonadhesive, open-mesh sheet material on said surface of the second portion of the adhesive tape tab, said openings of said sheet material defining the adhesive segments, each of said adhesive segments having an area so that the peel strength between said section portion of adhesive tape tab and said film over said segmented area is less than the tearing strength of said film over the same segmented area, but providing, on a combined basis with a plurality of similar adhesive segments, adequate holding strength of the adhesive tape tab to the diaper.

2. An adhesive tape tab as defined in claim 1 wherein the open-mesh sheet material is plastic.

3. An adhesive tape tab as defined in claim 2 wherein the plastic material is flat and sheet-like with a multiplicity of openings formed by filaments which are integrally joined at the intersections.

4. An adhesive tape tab as defined in claim 3 wherein the openings have an area less than 0.250 square inches, and wherein said filaments have a thickness between 0.002 and 0.012 inches.

5. An adhesive tape tab as defined in claim 1 wherein a segment at the furthest edge of the extendable second portion of tape has nonadhesive surfaces to act as a pull-tab to facilitate peeling after the second portion of the adhesive tape tab has been fastened to the outside film during use.

6. An adhesive tape tab as defined in claim 1 wherein a segment of nonadhesive, open-mesh sheet material extends beyond the furthest edge of the second portion of said adhesive tape tab to provide a pull-tab for peeling purposes.

7. An adhesive tape tab as defined in claim 1 wherein a segment of the second portion of said adhesive tape tab extends beyond the distal edge of the open sheet material and is folded back upon itself with the end portion of the open sheet material being interposed therebetween, the outside surfaces of said folded segment being nonadhesive whereby a pull-tab is formed.

* * * * *